US008247777B2

(12) United States Patent
Duraj et al.

(10) Patent No.: US 8,247,777 B2
(45) Date of Patent: Aug. 21, 2012

(54) SCINTILLATOR OPERATION AND CONTROL

(75) Inventors: Artan Duraj, Seven Hills, OH (US); John M. Frank, Hartville, OH (US)

(73) Assignee: Saint-Gobain Ceramics & Plastics, Inc, Worcester, MA (US)

( * ) Notice: Subject to any disclaimer, the term of this patent is extended or adjusted under 35 U.S.C. 154(b) by 0 days.

(21) Appl. No.: 13/418,119

(22) Filed: Mar. 12, 2012

(65) Prior Publication Data
US 2012/0168631 A1 Jul. 5, 2012

Related U.S. Application Data

(63) Continuation of application No. 13/160,010, filed on Jun. 14, 2011, now Pat. No. 8,164,062, which is a continuation of application No. 12/771,461, filed on Apr. 30, 2010, now Pat. No. 8,049,175.

(60) Provisional application No. 61/174,539, filed on May 1, 2009.

(51) Int. Cl.
*G01T 1/10* (2006.01)
(52) U.S. Cl. ....................................................... 250/362
(58) Field of Classification Search .................. 250/362, 250/361 R, 363.01–363.1; 378/98.8
See application file for complete search history.

(56) References Cited

U.S. PATENT DOCUMENTS

| 4,000,425 | A | 12/1976 | Craig |
| 4,245,157 | A | 1/1981 | Lewandowski |
| 5,640,016 | A | 6/1997 | Matsuda et al. |
| 5,651,047 | A | 7/1997 | Moorman et al. |
| 6,515,286 | B2 | 2/2003 | Kuwabara |
| 6,534,771 | B1 | 3/2003 | Rozsa |
| 6,895,077 | B2 | 5/2005 | Karellas et al. |
| 7,049,598 | B1 | 5/2006 | Jordanov et al. |
| 7,138,633 | B1 | 11/2006 | Rozsa et al. |
| 7,170,973 | B2 | 1/2007 | Gipp et al. |
| 7,180,068 | B1 | 2/2007 | Brecher et al. |
| 7,462,816 | B2 * | 12/2008 | Arseneau ................... 250/252.1 |
| 7,599,541 | B2 | 10/2009 | Hayashida |
| 7,850,367 | B2 | 12/2010 | Takenaka et al. |
| 2001/0039379 | A1 | 11/2001 | Hagelauer |
| 2004/0081278 | A1 | 4/2004 | Amemiya et al. |
| 2005/0175254 | A1 | 8/2005 | Granfors et al. |
| 2006/0104496 | A1 | 5/2006 | Arenson et al. |
| 2006/0118732 | A1 | 6/2006 | Blanton et al. |
| 2007/0223654 | A1 | 9/2007 | Aufrichtig et al. |
| 2009/0041189 | A1 | 2/2009 | Allison |

FOREIGN PATENT DOCUMENTS

JP 2004317300 A 11/2004

OTHER PUBLICATIONS

Saint-Gobain Crystals, Performance Resolution, Technical Information note Document #517, Downloaded on Apr. 30, 2010, 1 page.
Saint-Gobain Crystals, Scintillation Detector Operating Manual, Downloaded on Apr. 30, 2010, 13 pages.
Saint-Gobain Crystals, Scintillation Detector Operating Manual, 2004, 16 pages.
Z.B. Alfassi et al., On the elimination of the afterglow of CsI(TI) scintillation detector, Nuclear Instruments and Methods in Physics Research, 2009, pp. 585-588. vol. 606.
Saint-Gobain Crystals, Measuring Radiation: An Introductory Discussion, 2004, 12 pages.
Saint-Gobain Crystals, Scintillation Products, Scintillation Crystal Arrays and Assemblies, 2004, 8 pages.

* cited by examiner

*Primary Examiner* — Kiho Kim
(74) *Attorney, Agent, or Firm* — Abel Law Group, LLP; Christopher J. Cianciolo

(57) ABSTRACT

A method and system for reducing scintillator afterglow. Methods for reducing afterglow include conditioning a scintillator by exposing it to high flux densities of ionizing radiation. One technique includes operating an x-ray tube at elevated amperage.

20 Claims, 8 Drawing Sheets

| Test Date | CsI(Tl) Scintillator 100 mS Afterglow (ppm) | | | | | | |
|---|---|---|---|---|---|---|---|
| | 5644-5 | 4960-5 | 5649-5 | 4890-5 | 4895-5 | 4760-5 | |
| Day 1 pre-conditioning | 6346 | 9532 | 4642 | 4892 | 4751 | 9634 | |
| Day 1 post-conditioning | 2386 | 3266 | 2285 | 1720 | 1603 | 3368 | |
| Day 2 pre-conditioning | 3942 | 4375 | 3256 | 2486 | 2387 | 4850 | |
| Day 2 post-conditioning | 1237 | 1654 | 1135 | 839 | 831 | 1993 | |
| Day 3 pre-conditioning | 4587 | 4198 | 3728 | 2724 | 2477 | 4551 | |
| Day 3 post-conditioning | 2647 | 2926 | 2695 | 1962 | 1927 | 3454 | |
| Day 4 pre-conditioning | 6031 | 4236 | 4284 | 3221 | 2817 | 4551 | |
| Day 4 post-conditioning | 2418 | 2356 | 2325 | 1692 | 1560 | 2752 | |
| Day 5 pre-conditioning | 4673 | 3992 | 3913 | 2827 | 2515 | 4103 | |
| Day 5 post-conditioning | 2624 | 2590 | 2577 | 1846 | 1758 | 2966 | |
| Day 6 pre-conditioning | 4333 | 3660 | 3786 | 2879 | 2670 | 3899 | |
| Day 6 post-conditioning | 2687 | 2661 | 2707 | 1979 | 1894 | 2978 | |
| Day 7 pre-conditioning | 4017 | 3547 | 3626 | 2737 | 2476 | 3682 | |
| Day 7 post-conditioning | 2159 | 1999 | 2000 | 1446 | 1242 | 2187 | |
| Day 8 pre-conditioning | 4057 | 3667 | 3764 | 2846 | 2494 | 3676 | |
| Day 8 post-conditioning | 2495 | 2361 | 2373 | 1739 | 1618 | 2606 | |

FIG. 2

SCINTILLATOR OPERATION AND CONTROL

CROSS-REFERENCE TO RELATED APPLICATIONS

This application claims priority under 35 U.S.C. §120 and is a continuation of U.S. patent application Ser. No. 13/160,010 entitled "Scintillator Operation and Control" by Duraj et al., filed on Jun. 14, 2011, which claims priority under 35 U.S.C. §120 and is a continuation of U.S. patent application Ser. No. 12/771,461 entitled "Scintillator Operation and Control" by Duraj et al., filed on Apr. 30, 2010, now U.S. Pat. No. 8,049,175, which claims the benefit under 35 U.S.C. §119(e) of U.S. Provisional Patent Application No. 61/174,539 entitled "Scintillator Operation and Control" by Duraj et al., filed on May 1, 2009. Each patent and patent application cited herein is hereby incorporated by reference in its entirety.

FIELD OF THE INVENTION

The present invention relates generally to scintillators, and more particularly to the operation of systems that include scintillators.

BACKGROUND

Scintillators, or scintillation devices, are used in diagnostic instrumentation to convert ionizing radiation into more easily detectable and imageable light. "Scintillator" is used herein to mean any substance that emits light in the visible or infrared range in response to incident ionizing radiation. During operation of a scintillation system, a radiation source emitting excitatory radiation is typically directed at a subject, e.g., a patient or an object, and the resulting radiation pattern is guided to a scintillator where photons in the visible or infrared range are emitted in response to the ionizing radiation. The resulting photons can then be detected by a photodetector such as a photodiode, photo multiplier tube, or charge-coupled device. The radiation source may be, for instance, x-rays, gamma rays, alpha particles, or beta particles. The radiation may be generated electrically or emitted from a radioactive isotope.

Scintillators may be polymers or crystals that are substantially transparent to the output wavelength. Instruments that include scintillators are used in a variety of industries, including healthcare, security screening, and mining. Diagnostic and analytical methods include x-ray fluoroscopy, computed radiography, digital radiography, radio gauging (RG), single photon emission computed tomography (SPECT), positron emission tomography (PET), and computed tomography (CT).

SUMMARY OF THE INVENTION

Methods and systems are provided for reducing the afterglow of a scintillator. Methods may be computer implemented.

In one aspect, a method of operating a scintillation device is provided, the method comprising applying current to a source to irradiate a scintillator at a first flux; and subsequently adjusting the current to irradiate the scintillator at a second flux that is greater than zero and less than or equal to 20% of the first flux.

In another aspect, a computer executable medium encoded with software that, when executed by a computer, causes the computer to carry out a process for performing a method of operating a scintillation device is provided, the method comprising applying current to a source to irradiate a scintillator at a first flux; and subsequently adjusting the current to irradiate the scintillator at a second flux that is greater than zero and less than or equal to 20% of the first flux.

In one aspect, a method of operating a scintillation device is provided, the method comprising applying current to an x-ray tube to irradiate a scintillator at a first flux; and subsequently adjusting the current to irradiate the scintillator at a second flux that is greater than zero and less than or equal to 50% of the first flux.

In another aspect, a method of conditioning a scintillator is provided, the method comprising applying current to an ionizing radiation source during a conditioning period at a first amperage that is greater than a second amperage applied to the radiation source during imaging operation, and irradiating the scintillator during the conditioning period.

In another aspect, a method of conditioning a scintillator is provided, the method comprising irradiating a scintillator at a first radiation flux density for a conditioning period and irradiating the scintillator at a second flux density for an operating period wherein the first flux density is more than two times the second flux density.

In another aspect, a method of reducing the afterglow of a scintillator in an analytical instrument including an x-ray source is provided, the method comprising irradiating the scintillator at a first flux density for a first time period, irradiating the scintillator at a second flux density for a second time period during which images of a subject are provided, wherein the first flux density is at least twice that of the second flux density, and reducing by a factor of at least two the afterglow of the scintillator during the second time period when compared to the afterglow of the scintillator when the first time period is not practiced.

In another aspect, an x-ray based diagnostic apparatus is provided, the apparatus comprising an x-ray source, a scintillator, a photodetector, and a controller having at least a first setting and a second setting wherein the first setting provides a first electric current to the x-ray source for a time period of at least one minute and the second setting provides a second electric current to the x-ray source, the first electric current being at least twice the amperage of the second electric current.

The features and advantages described herein are not all-inclusive, and, in particular, many additional features and advantages will be apparent to one of ordinary skill in the art in view of the drawings, specification, and claims. Moreover, it should be noted that the language used in the specification has been selected principally for readability and instructional purposes, and not to limit the scope of the inventive subject matter.

BRIEF DESCRIPTION OF THE DRAWINGS

The above-mentioned and other features of this disclosure, and the manner of attaining them, will become more apparent and better understood by reference to the following description of embodiments described herein taken in conjunction with the accompanying drawings, wherein:

FIG. 2 is a table providing afterglow readings for one embodiment;

DETAILED DESCRIPTION

In one aspect, a process for reducing the afterglow from a scintillator is described. In one set of embodiments, the scintillator can be exposed to a high flux level for a conditioning period prior to using the scintillation device. To obtain this increase in flux, the system's radiation source, such as an x-ray tube, can be operated at elevated current for a period of time prior to standard analytical operation of the system. The amperage through the x-ray tube (and/or the flux) may be greater than two times, five times, or ten times the amperage supplied to the device at standard operating levels. During this conditioning period, the scintillator may be exposed to a high flux density of ionizing radiation after which afterglow is reduced (at operating current levels), providing for improved imaging and analytical characteristics. Afterglow reduction may be implemented without chemically altering the scintillators and without physical changes to the scanning instrument in which the scintillator is installed.

Afterglow can occur when the light output from a scintillator does not stop immediately upon cessation of incident ionizing radiation. If the energy of a pulse is measured over time, it may exhibit a rate of decay that results in a tail that can last for microseconds, milliseconds, or even seconds after the excitatory radiation has stopped impacting the scintillator. One reason for this afterglow is that some of the transitions from ionizing radiation to visible light occur with different rates of decay. The lower rates of decay can result in afterglow, and this afterglow can result in artifacts that may cause, for example, slower responding detectors, inaccurate dimensional measurements (in RG), reduced contrast in images, and image ghosting. A reduction in afterglow, therefore, can result in faster scanning, more accurate measurements, and better image quality. Afterglow can differ significantly with different types of scintillators.

Figure 1:
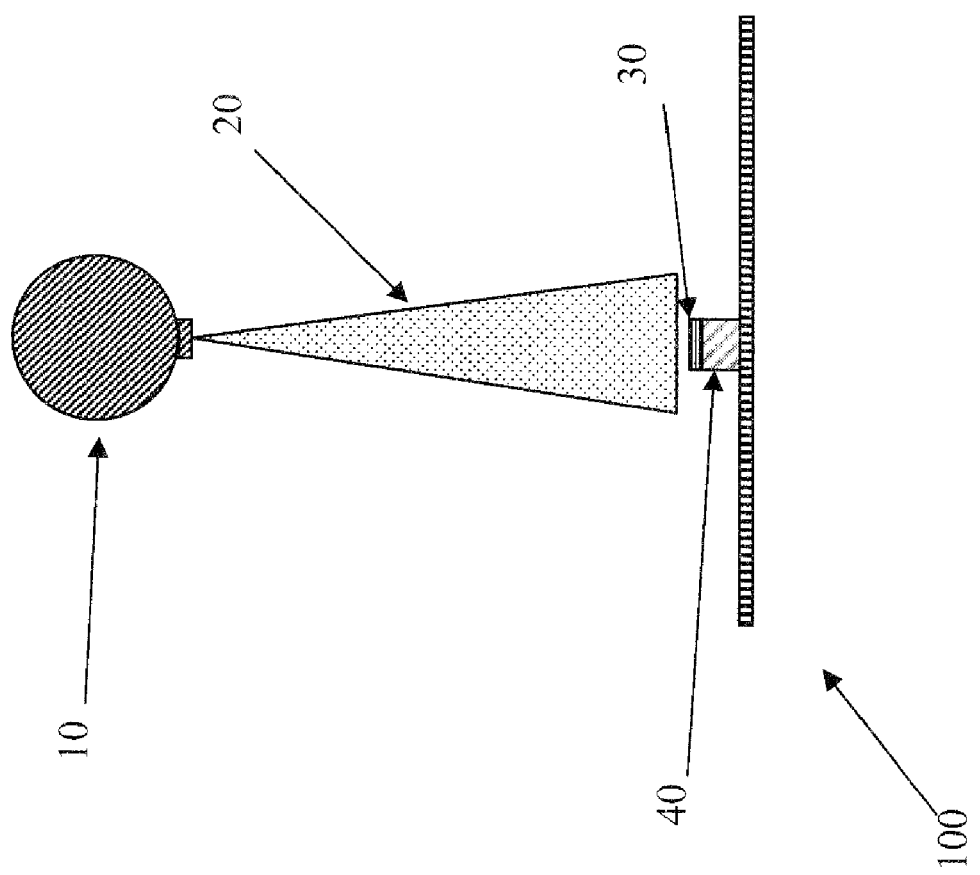
FIG. 1 is a schematic of one embodiment of a scintillation system.

An embodiment of a scintillation system is illustrated in FIG. 1. System 100 includes x-ray tube 10 that also may be an alternate source of ionizing radiation. Radiation source 10 emits radiation beam 20 that impacts scintillator 30. Scintillator 30 receives ionizing radiation and in response emits light in the visible or infrared region that is in turn detected by photodetector 40, which may be a photodiode or photomultiplier tube (PMT). Photodetector 40 converts light into an electrical signal that can be processed to produce an image. Scintillator 30 is exposed to a radiation flux density that can be controlled by varying the current supplied to x-ray tube 10. An increase in amperage supplied to the x-ray tube results in an increase in radiation flux density.

Scintillators may include any substance that emits light in the visible or infrared range in response to incident ionizing radiation. Scintillators can include, for example, inorganic crystals, organic crystals, and polymers. Some examples of crystal scintillators are cesium iodide (CsI), thallium-doped cesium iodide (CsI(Tl)), bismuth germanate (BGO), thallium-doped sodium iodide (NaI(Tl)), barium fluoride ($BaF_2$), europium-doped calcium fluoride ($CaF_2(Eu)$), cadmium tungstate ($CdWO_4$), cerium-doped lanthanum chloride ($LaCl_3(Ce)$), cerium-doped lutetium yttria silicates ($LuYSiO_5(Ce)$), silver-doped zinc sulfide (ZnS(ag)), and yttrium aluminum garnet ($Y_3Al_5O_{12}(Ce)$). Crystals may be polycrystalline or single crystal in nature.

Cesium iodide scintillators such as cesium iodide crystals with a thallium activator (CsI(Tl)) exhibit many properties that make them useful as scintillators, primarily because of the good light output provided by these crystals. When compared to alternatives such as cadmium tungstate ($CdWO_4$), however, the afterglow from CsI(Tl) can be significantly greater. Various compositions and devices exist for reducing afterglow from CsI(Tl) scintillators. For example, afterglow can be compensated for by using light filters, such as those described in APPARATUS EMPLOYING A FILTERED SCINTILLATOR AND METHOD OF USING SAME, U.S. Pat. No. 7,138,633, which is incorporated by reference herein. Afterglow also can be partially addressed by altering the composition of the crystal, such as by reducing impurities or by the addition of lanthanide series elements as disclosed in SCINTILLATION MATERIALS WITH REDUCED AFTERGLOW AND METHOD OF PREPARATION, U.S. Pat. No. 7,180,068, which also is incorporated by reference herein.

A conditioning period is a period of time over which a scintillation crystal is exposed to an ionizing radiation flux that is greater than the exposure realized during a standard operating period. The source of ionizing radiation may be the same as or different from the source that is used during standard operation. For instance, during a conditioning period an x-ray tube may be operated at a first, higher amperage to increase the amount of radiation impacting the scintillator and then, during a standard operating period, may be operated later at a second, lower amperage. Alternatively, one or more x-ray sources may be used for conditioning, and an alternative source may be used for operation. The resulting reduction in afterglow may not be permanent and may last for more than one hour, more than 4 hours, more than 8 hours, or more than 24 hours. The amount of afterglow reduction may decrease slowly over time if the scintillator is not reconditioned. The period of reduction may be partially dependent on the level of use of the scintillator after the conditioning period. A higher level of use, e.g., greater radiation flux or a greater exposure time, may result in extending the period of afterglow reduction. The conditioning period may be repeated as needed. For instance, the afterglow effect can be evaluated or monitored, and when afterglow increases to a threshold value, the conditioning procedure can be repeated. The procedure may be automated through the use of a programmable controller or may be initiated by an operator. An indicator may be triggered by the system to prompt the operator to re-condition the scintillator. Triggering may be based, for example, on afterglow values or elapsed time.

A baseline level of afterglow may be set by measuring the amount of afterglow at a set time period, for example, 100 mS after the x-ray tube has been turned off and the output has dropped to 50% of its peak value. This baseline level can be measured at standard operating levels of radiation flux density (without a conditioning period). For instance, with an x-ray source, a baseline may be determined at standard (operating) voltage and current settings, such as 140 kV at 0.5 mA. By conditioning the scintillator, the afterglow may be reduced by more than 20%, 30%, 50%, 60%, or 70%. This means that after conditioning, the afterglow will be reduced by these amounts (compared to the baseline level) during standard operation. Afterglow values may be reported in parts per million (ppm) or percentage, as is known to those of skill in the art. Afterglow in ppm at time $t_1$ is calculated by using the equation: (light output at $t_1$)/(light output at operational current and voltage)×$10^6$. In some embodiments the absolute afterglow reduction at 100 mS (i.e., 100 mS after time $t_0$ when the x-ray tube has been turned off and light output has decreased to 50% of peak value) may be greater than 1000, greater than 2000, or greater than 3000 ppm.

After conditioning, a reduction in afterglow may be apparent over short, intermediate, and long time intervals. For instance, effective afterglow reduction has been demonstrated when measured at 20 mS, 100 mS, 200 mS, 300 mS, 500 mS, 750 mS, 1000 mS, and 2000 mS.

A conditioning period may proceed for a period sufficient to achieve the desired reduction in afterglow. The period may vary, for example, with scintillator composition and with the radiation flux density to which the scintillator is exposed. For some scintillation crystals, including alkali halide scintillators such as CsI(Tl), the conditioning period may be greater than one minute, greater than 2 minutes, greater than 5 minutes, greater than 10 minutes, greater than 30 minutes, or greater than 60 minutes. Appropriate conditioning periods for various scintillators and systems can be determined by conditioning for increasing lengths of time at a given radiation flux density and determining the point at which the reduction in afterglow due to increased time provides diminishing returns. Likewise, an appropriate radiation flux density for conditioning can be determined by choosing a fixed time period and measuring the marginal decrease in afterglow that corresponds to a marginal increase in radiation flux density over the fixed time period. Radiation flux density may be controlled, for example, by controlling the current to an x-ray tube. In such a case, the conditioning current may be, for example, two times, five times, or ten times the amperage applied during standard operation.

In another aspect, a scintillation system can be configured to condition a scintillator. Any system incorporating a scintillator, such as a luggage scanner, medical scanner, or geotechnical scanner, can be programmed or constructed to include a conditioning step. Instructions for conditioning can be provided on a computer executable medium such as a hard drive. Instructions may include, for example, providing an increased radiation flux density to a scintillator for a predetermined amount of time, such as one minute, five minutes, 30 minutes, or one hour. This may include providing current to an x-ray tube at elevated amperage. Steps for closing a shutter or otherwise isolating the radiation beam during conditioning may be used. Additional steps may include providing a reminder to the operator that a conditioning procedure is due or overdue. Systems may include indicators, such as indicator lights or display readouts that provide notice regarding the status of a conditioning step and/or the readiness of the system for standard operation.

Conditioning may be useful with a variety of scintillators including those comprised of alkali halides. Specific alkali halide scintillators include, but are not limited to, CsI, CsI(Tl), CsI(Na), $CdWO_4$, and $BaF_2$. The efficacy of a conditioning period when applied to other scintillators can be evaluated by using the procedures described herein for determining appropriate levels of radiation flux density and/or appropriate periods of time at elevated flux density levels. Systems with which this technology may be useful include, for example, x-ray fluoroscopy, computed radiography, digital radiography, radio gauging (RG), single photon emission computed tomography (SPECT), positron emission tomography (PET), and computed tomography (CT).

A series of experiments was completed to determine the efficacy of one embodiment of a conditioning technique. A series of CsI(Tl) scintillation crystals were prepared and exposed to various x-ray flux densities using an Analogic Test system model AN2K-DTS. The instrument was fitted with a Pantak Seifert ISOVOLT 160 M2/0.4-1.5 x-ray tube and Hamamatsu S1337-1010BR photodiodes. Temperature and relative humidity were kept constant at about 23° C. and 30% respectively. Afterglow levels were measured with and without conditioning.

Duplicate crystals were cut with a wire saw from each of six different ingots of CsI(Tl). Afterglow for each crystal was measured twice each weekday for several months. The first afterglow measurement was taken prior to conditioning, and the second measurement was taken after completion of the conditioning period. Conditioning consisted of irradiating the crystal for 60 minutes at 140 kV and 5 mA (10× the standard amperage) for the entire conditioning period. Afterglow readings were recorded under standard operating conditions of 140 kV and 0.5 mA. Light output at 140 kV and 0.5 mA was consistent throughout the period of the test. To measure afterglow, the x-ray tube was turned off and the timer started when the detector realized a drop of 50% in peak intensity. Measured time intervals included 20 mS, 100 mS, 200 mS, 300 mS, 500 mS, 750 mS, 1000 mS, and 2000 mS. Each reading was actually the average of 10 sequential readings clustered around the end of the specific time interval. Results showed a decrease in afterglow of more than 50%, more than 60%, and more than 75%.

FIG. 2 is a table providing 100 mS results for 8 days of tests on 6 different CsI(Tl) crystals. Each crystal exhibited a reduction in afterglow of at least 50% (factor of 2) after the one-hour conditioning period. A second batch of crystals showed similar results.

Figure 3:
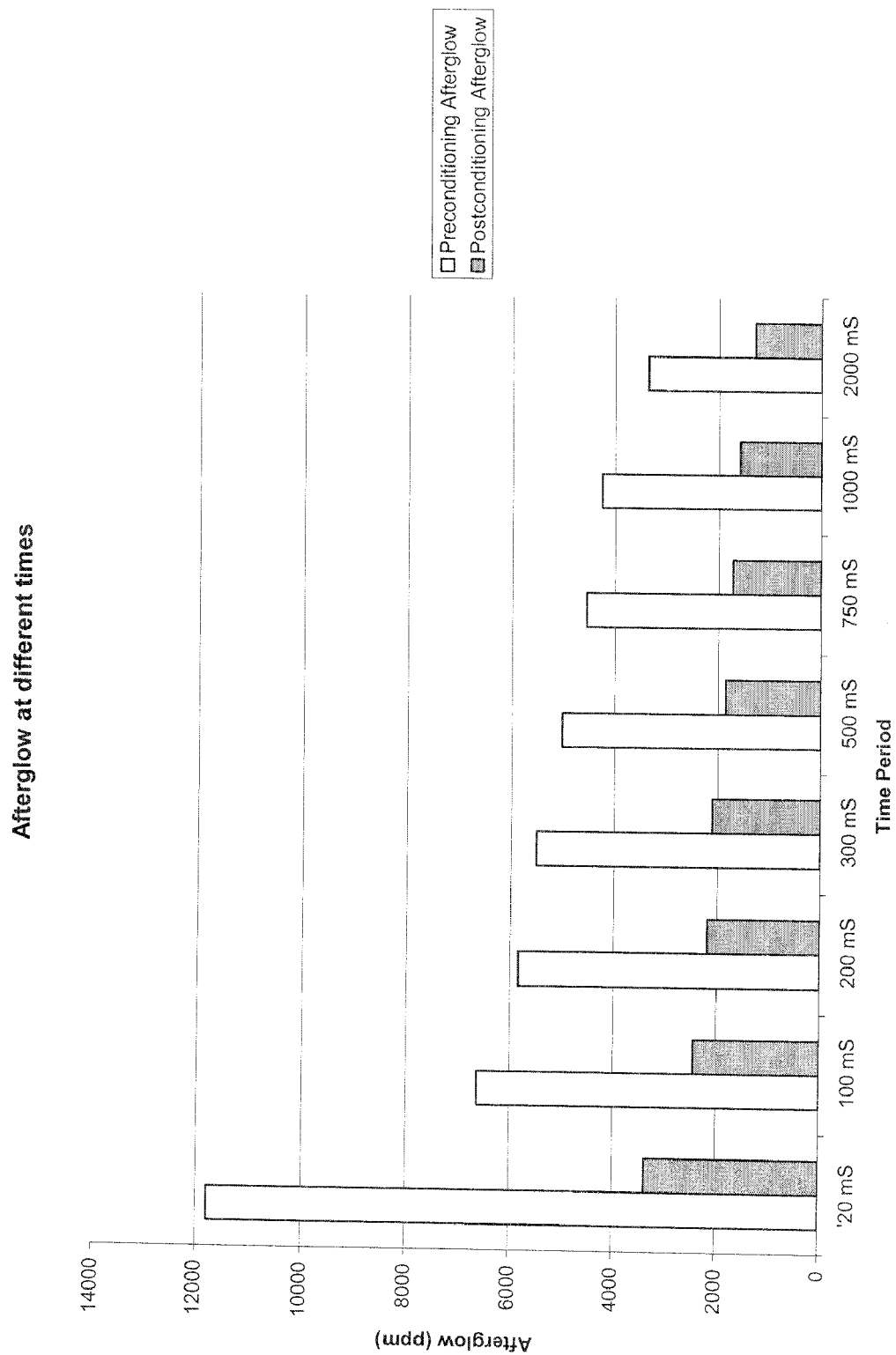
FIG. 3 is a bar graph illustrating afterglow reduction in one embodiment.

FIG. 3 is a bar graph comparing pre- and post-conditioning afterglow at eight different afterglow times. Each of six different crystals was tested at each of the eight time intervals prior to conditioning by irradiating each crystal while positioned over two separate, but identical, photodiodes. This provided twelve data points (two photodiodes for each of six crystals) that were averaged to provide the plotted values (pre-conditioned). The procedure was repeated after conditioning for one hour at 140 kV and 5 mA (post-conditioned). Results indicate an extensive reduction (>50%) in afterglow over the entire time period from 20 mS to 2000 mS. Light Output averaged 648,424 pre-conditioned and 628,945 post-conditioned.

Figure 4:
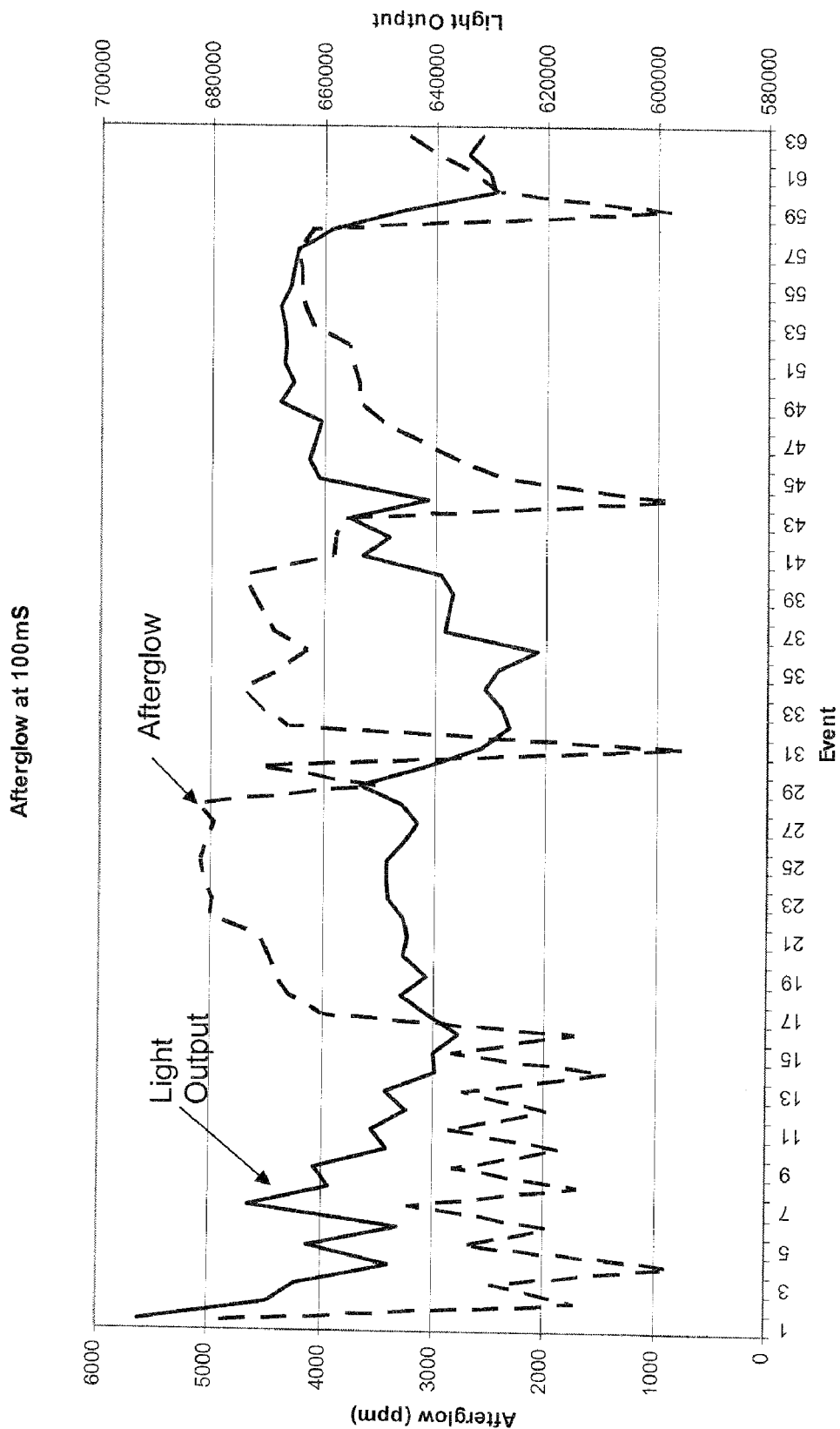
FIG. 4 is a trend line showing afterglow readings for one embodiment.

FIG. 4 illustrates the trend over a 50-day period for a representative CsI(Tl) scintillator (4890-5). For the first eight days, two 100 mS afterglow measurements were obtained each day. The first was prior to any conditioning for that day, and the second was after conditioning. After the initial eight day period (event 16), the scintillator was conditioned once about every 3 weeks. A sharp drop in afterglow values can be seen whenever the scintillator was conditioned, e.g., at events 2, 4, 6, 8, 10, 12, 14, 16, 31, 44, and 59. In the absence of conditioning, afterglow values increased to their original levels within two or three days with the system being tested daily under standard operating conditions. FIG. 4 also provides the light output for scintillator 4890-5 over the same time period and indicates no significant decrease in light output over time.

Figure 5:
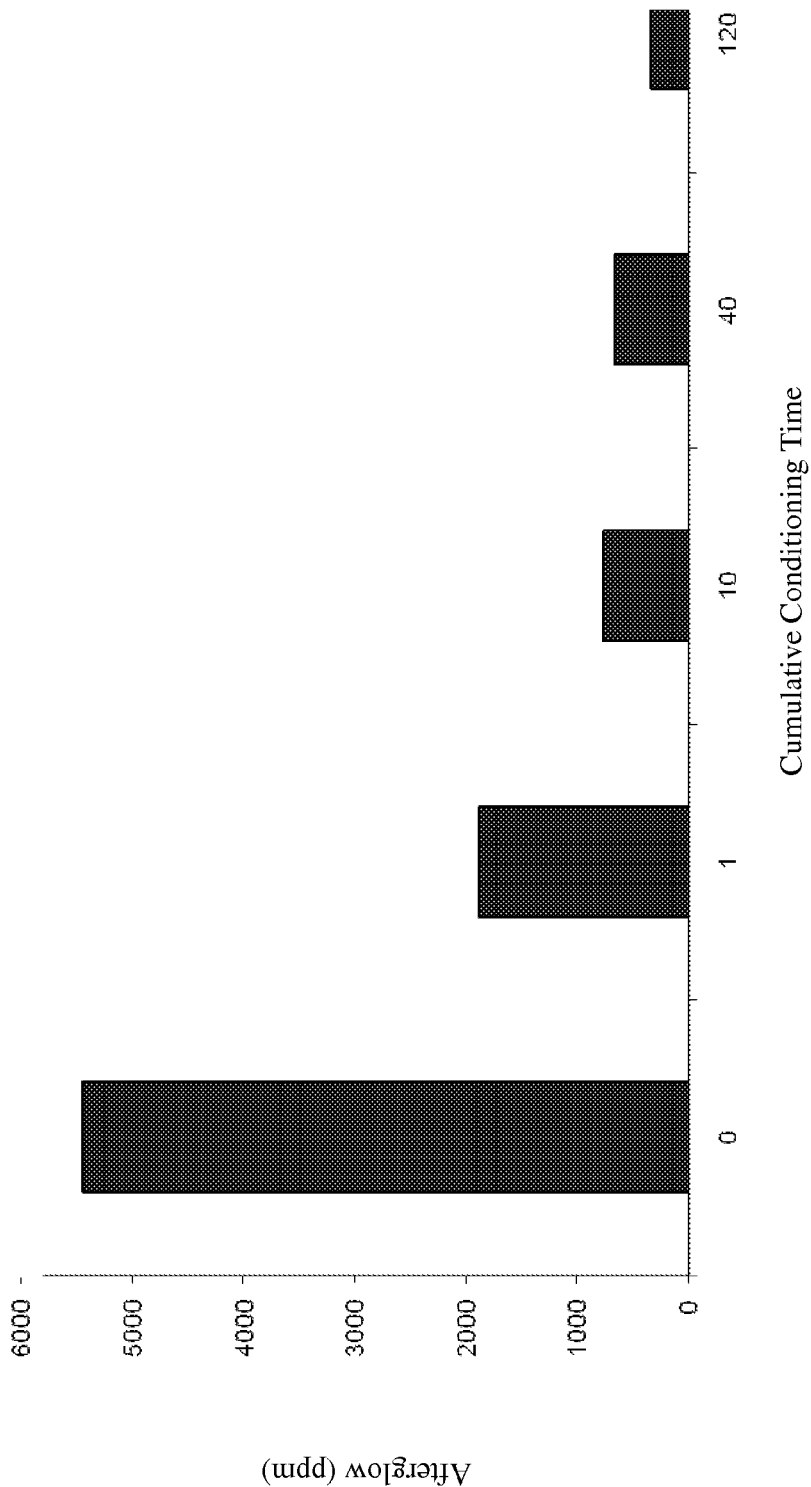
FIG. 5 is a bar graph illustrating 100 ms afterglow readings at cumulative conditioning times.

In another experiment, the conditioning time (exposure) was increased to determine the effect that cumulative conditioning has on the reduction of afterglow. The same AN2K-DTS instrument and procedures were used as described above. Six different CsI(Tl) scintillators were conditioned for successively longer periods of time, and afterglow was measured at 100 mS after completion of each successive conditioning period. In order to reduce any effect of DC offset, the system was allowed a recovery period of one to two minutes after each measurement before additional conditioning was re-started. With no conditioning exposure, the average afterglow from the six crystals was 5451 ppm. Each of the six crystals was then evaluated for afterglow after an exposure of one minute, and the readings from 2 channels for each crystal were averaged to obtain an average afterglow (for all six crystals) of 1882 ppm. After a cumulative 10 minutes exposure, the average afterglow was 768 ppm. After a cumulative 40 minutes of exposure, the average afterglow was 674 ppm. After a cumulative 120 minutes of exposure, the average afterglow was 342 ppm. Average results are provided in graphical form in FIG. 5. The results indicate that the conditioning effect occurs at exposure times of one minute or less, and appears to improve significantly up to about 10 minutes and somewhat marginally thereafter up to two hours.

Figure 6:
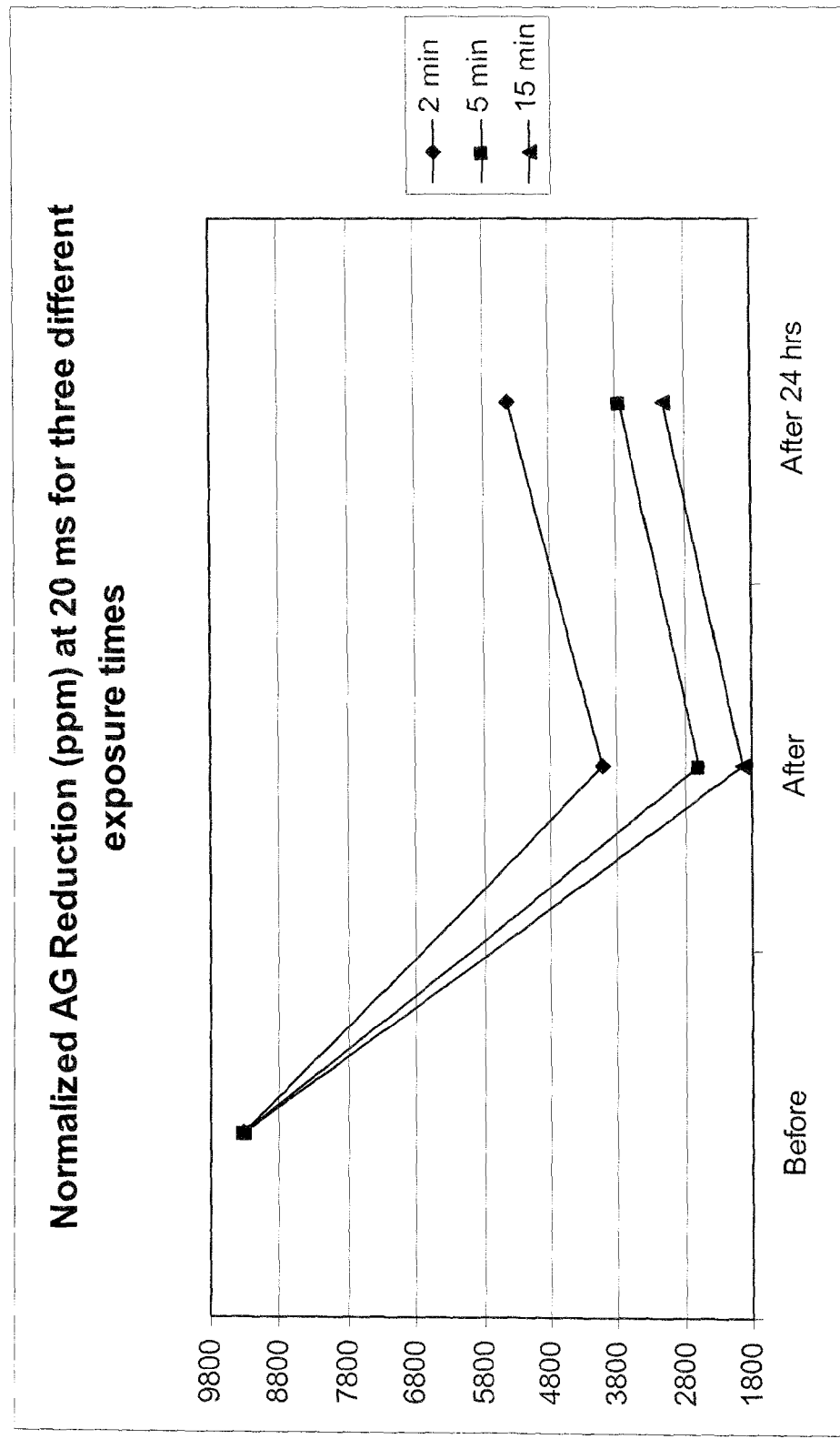
FIG. 6 is a graph providing 20 ms afterglow readings before, immediately after, and 24 hours after conditioning for different conditioning times.
Figure 7:
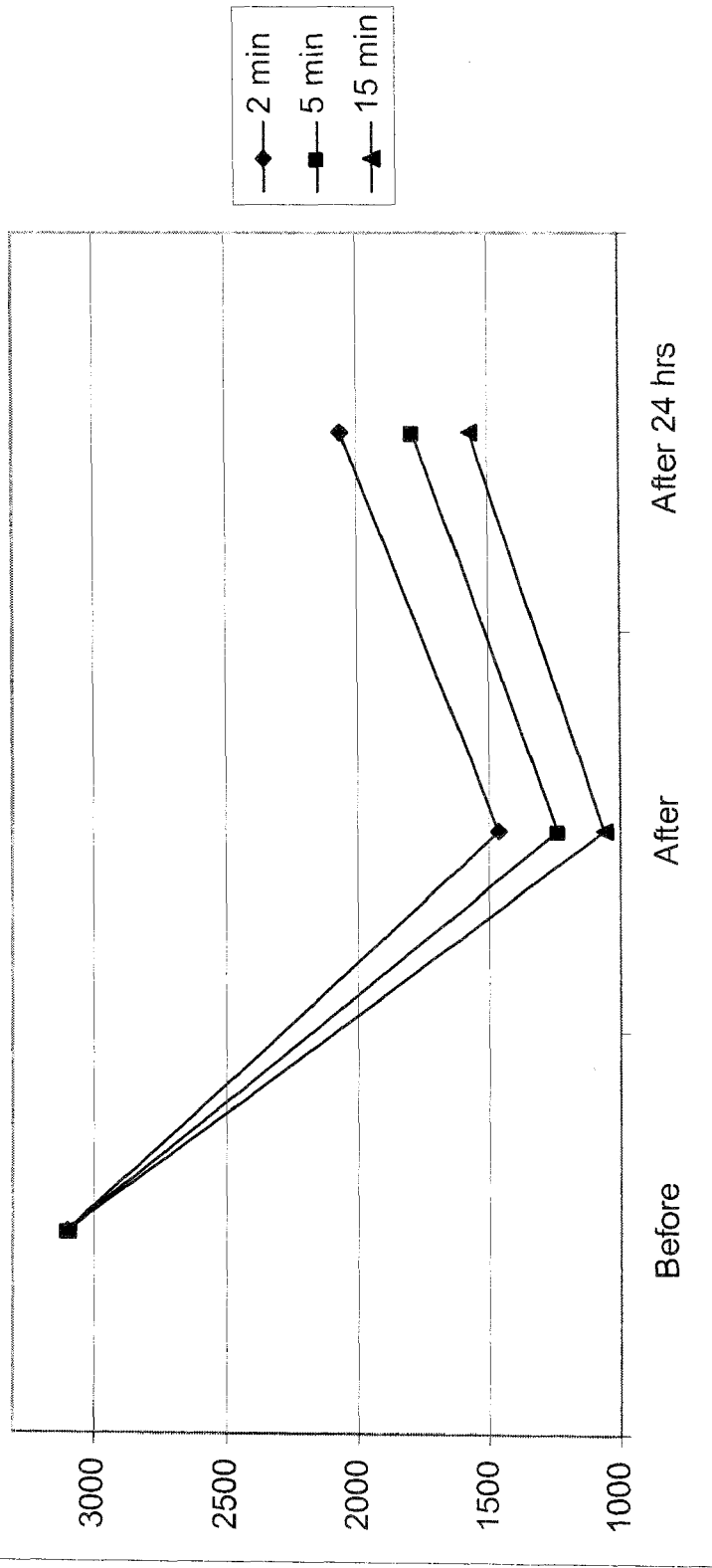
FIG. 7 is a graph providing 100 ms afterglow readings before, immediately after, and 24 hours after conditioning for different conditioning times.

Additional tests were run on arrays of CsI(Tl) crystals (as used in airport luggage screeners) to compare the afterglow effects immediately after conditioning and 24 hours after the conditioning process. The conditioning process included subjecting the crystals to a radiation flux of 140 kV at 5 mA for three different time periods of 15 minutes, 5 minutes, and 2 minutes. Afterglow readings were then taken for each group using the AN2K-DTS instrument at time intervals of 20 ms and 100 ms. Instrument settings for the afterglow (AG) readings were 120 kV, 1 mA, gain of 50 μC, and int time of 1 ms. Results at 20 ms and at 100 ms are depicted graphically in FIGS. 6 and 7, respectively. The data include afterglow readings in ppm before treatment, immediately after treatment, and 24 hours after treatment. Results indicate a consistent partial rebound in afterglow readings at 24 hours. This indicates that in practice the CsI(Tl) crystals may be re-treated on a regular schedule, for instance daily, to avoid afterglow creep that occurs in this time frame. The results also show an improvement in absolute afterglow reduction as treatment exposure time is increased from 2 minutes to 5 minutes to 15 minutes.

Figure 8:
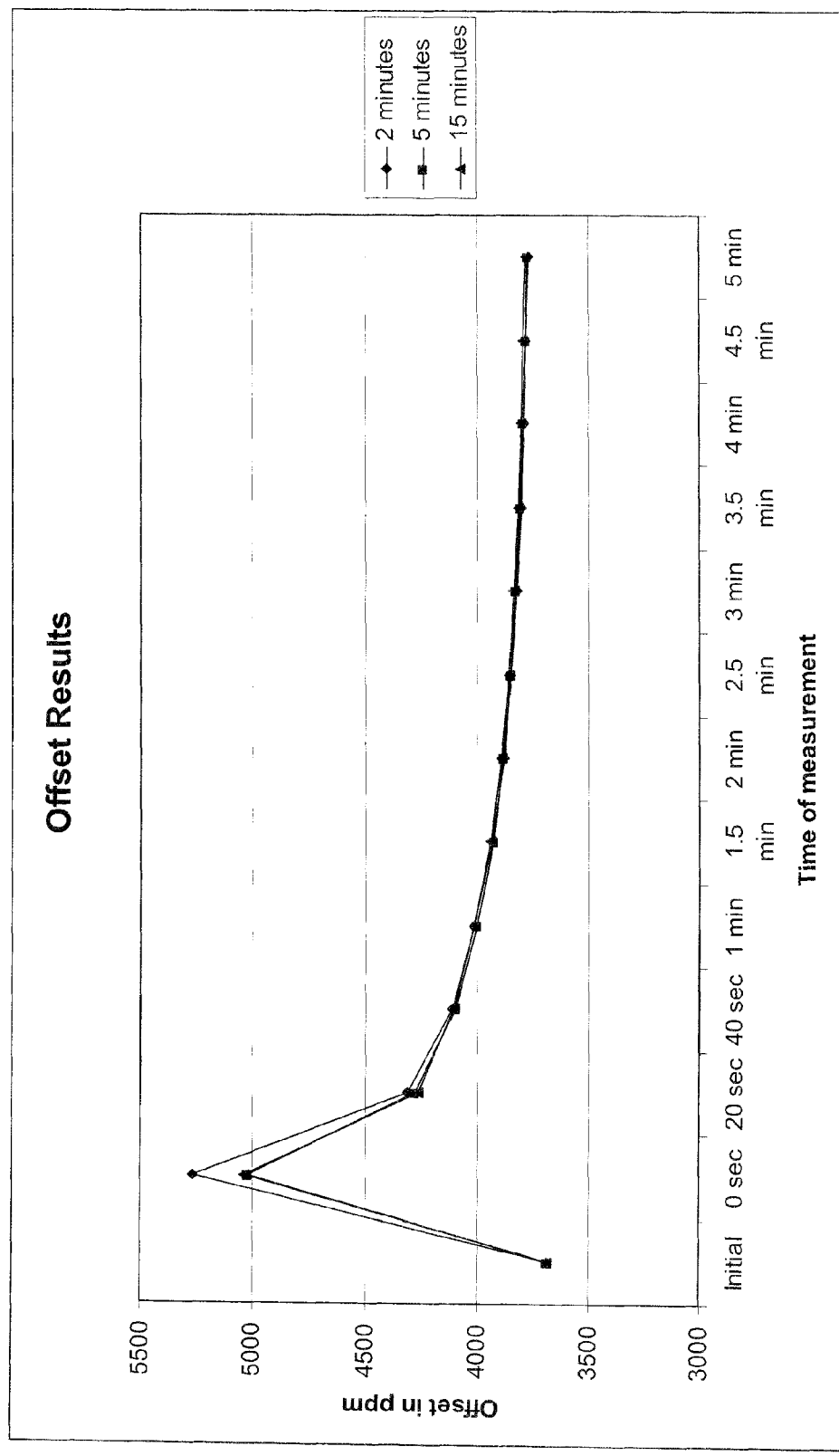
FIG. 8 provides offset results at increasing time intervals.

An additional experiment was performed to determine whether some or all of the reduction in afterglow could be attributed to "offset" that occurs after treatment at high flux levels. Offset is a long-term afterglow effect that can last for multiple seconds or minutes after a crystal is irradiated. Offset can be compensated for if it is consistent over time, and can be substantially ignored if it tails off quickly after initial exposure to high flux. In this experiment, the same type of CsI(Tl) crystals as described above were treated at 140 kV and 5 mA for periods of 2, 5, and 15 minutes. Without further excitement of the crystals, light output was recorded immediately after shut off and at 30 second intervals thereafter for five minutes. Results are shown graphically in FIG. 8 and indicate that an initially high offset of about 1300 ppm above baseline quickly declines to a level close to baseline within a matter of minutes. Different exposure times (2 min, 5 min, and 15 min) at the high flux level showed insignificant changes in offset, particularly when measured after 1 minute or longer. Therefore, treatment methods using exposure to high levels of flux can be reliably implemented without regard to offset, particularly if a waiting period of about 1 minute is implemented after the treatment exposure and before imaging takes place.

While several embodiments of the present invention have been described and illustrated herein, those of ordinary skill in the art readily will envision a variety of other means and/or structures for performing the functions and/or obtaining the results and/or one or more of the advantages described herein, and each of such variations and/or modifications is deemed to be within the scope of the present invention. More generally, those skilled in the art readily will appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified, unless clearly indicated to the contrary.

All references, patents and patent applications and publications that are cited or referred to in this application are incorporated in their entirety herein by reference.

What is claimed is:

1. An apparatus comprising:
  a radiation source;
  a scintillator configured to receive radiation from the radiation source; and
  a controller having:
    a conditioning mode to control the radiation source to emit radiation at a first radiation flux to condition the scintillator; and
    an imaging mode to control the radiation source to emit radiation at a second radiation flux that is less than the first radiation flux during an imaging operation.

2. The apparatus of claim 1, wherein the first radiation flux is at least twice the second radiation flux.

3. The apparatus of claim 1, wherein the controller is configured to control current supplied to the radiation source, wherein the current supplied to the radiation source for the conditioning mode is at least twice the current supplied to the radiation source for the imaging mode.

4. The apparatus of claim 1, wherein the scintillator comprises an alkali halide.

5. The apparatus of claim 1, wherein the scintillator comprises cesium iodide and a thallium activator.

6. The apparatus of claim 1, further comprising a photodetector to convert a light pulse from the scintillator to an electronic pulse, wherein the scintillator is disposed between the radiation source and the photodetector.

7. The apparatus of claim 1, wherein the radiation source comprises an x-ray tube.

8. The apparatus of claim 1, the apparatus comprises a luggage scanner, or a medical scanner, or a geotechnical scanner.

9. The apparatus of claim 1, wherein the apparatus is a x-ray fluoroscopy apparatus, a computed radiography apparatus, a digital radiography apparatus, a radio gauging apparatus, a positron emission tomography apparatus, or a computed tomography apparatus.

10. The apparatus of claim 9, wherein the computed tomography apparatus is a single photon emission computed tomography apparatus.

11. A tangible, computer executable medium having code that, when executed by a controller, causes the controller to carry out a method of operating an apparatus comprising a radiation source, a scintillator, and the controller, wherein the method comprises:
   conditioning the scintillator by controlling the radiation source to produce a first radiation flux; and
   irradiating the scintillator at a second radiation flux during an imaging operation, wherein the first radiation flux is greater than the second radiation flux.

12. The tangible, computer executable medium of claim 11, wherein the method further comprises determining whether a predetermined time period has elapsed in which the scintillator has not been conditioned.

13. The tangible, computer executable medium of claim 12, wherein the method further comprises sending a reminder to an operator of the apparatus that a conditioning procedure is due or overdue.

14. The tangible, computer executable medium of claim 12, wherein the method further comprises conditioning the scintillator for a second time at least partly in response to determining that the predetermined time period has elapsed.

15. The tangible, computer executable medium of claim 11, wherein the method further includes selecting a particular value for a conditioning parameter based at least in part on a composition of the scintillator.

16. The tangible, computer executable medium of claim 15, wherein, as compared to the scintillator, a different scintillator having a different composition has a different value for the conditioning parameter.

17. The tangible, computer executable medium of claim 11, wherein the method further comprises:
   determining a baseline level of afterglow of the scintillator; and
   determining a post-conditioning afterglow of the scintillator to confirm the afterglow does not exceed the baseline level of afterglow.

18. The tangible, computer executable medium of claim 17, wherein:
   determining the baseline level of afterglow is determined after the radiation source has been powered down for more than 8 hours and before conditioning the scintillator; and
   determining a post-conditioning afterglow of the scintillator is performed no more than 24 hours after conditioning the scintillator.

19. The tangible, computer executable medium of claim 11, wherein conditioning reduces an afterglow of the scintillator by more than 20%.

20. The tangible, computer executable medium of claim 11, wherein the method further comprises isolating a radiation beam from the radiation source during conditioning.

* * * * *